United States Patent [19]

VandenBerg

[11] Patent Number: Plant 7,488

[45] Date of Patent: Apr. 2, 1991

[54] CHRYSANTHEMUM PLANT NAMED NAPLES

[75] Inventor: Cornelis P. VandenBerg, Salinas, Calif.

[73] Assignee: Yoder Brothers, Inc., Barberton, Ohio

[21] Appl. No.: 481,068

[22] Filed: Feb. 16, 1990

[51] Int. Cl.[5] ..... A01H 5/00

[52] U.S. Cl. ..... Plt./77

[58] Field of Search ..... Plt./77, 78, 76

*Primary Examiner*—Howard J. Locker
*Attorney, Agent, or Firm*—Foley & Lardner, Schwartz, Jeffery, Schwaab, Mack, Blumenthal & Evans

[57] ABSTRACT

A Chrysanthemum plant named Naples particularly characterized by its flat capitulum form; decorative capitulum type; white ray floret color, with a cream center of the flower and a cream flower bud; diameter across face of capitulum of 70 to 80 mm when fully opened; flowering response in Salinas, Calif. under normal temperatures is 51 to 55 days after start of short days; peduncle length of first lateral ranging from 10 to 15 cm, of the fourth lateral from 15 to 20 cm on open, terminal sprays; and a plant height of 81 to 85 cm when grown as a single stem cut mum in Salinas, Calif. with 6 to 8 long days prior to start of short days.

3 Drawing Sheets

The present invention comprises a new and distinct cultivar of Chrysanthemum, botanically known as *Dendranthema grandiflora,* and referred to by the cultivar name Naples.

Naples, identified as 85-268009, was originated by the inventor Cornelis P. VandenBerg from a cross made in a controlled breeding program in Salinas, Calif., in 1984.

The female parent of Naples was an unnamed seedling identified as 81-671002, a yellow decorative cut spray mum. The male parent of Naples was also an unnamed seedling, identified as 82-J38047, a white decorative cut spray mum with a high number of disc florets.

Naples was discovered and selected as one flowering plant with the progeny of the stated cross by Cornelis P. Vandenberg in March 1986, in a controlled environment in Salinas, Calif.

The first act of asexual reproduction of Naples was accomplished when vegetative cuttings were taken from the initial selection in May 1986 in a controlled environment in Salinas, Calif., by technicians working under the supervision of Cornelis P. VandenBerg.

Horticultural examination of controlled flowerings of successive plantings has shown that the unique combination of characteristics as herein disclosed for Naples are firmly fixed and are retained through successive generations of asexual reproduction.

Naples has not been observed under all possible environmental conditions. The phenotype may vary significantly with variations in environment such as temperature, light intensity and daylength. For example, plant height will increase with an increased number of long days after planting prior to start of short days. Under low night temperatures (10 degrees Celsius and lower) flowering can be expected to be delayed. Under high temperatures (25 degrees Celsius night and 35 degrees Celsius day) flowering can be expected to be delayed and be more uneven than under normal temperatures. Normal temperatures can be described as 15 degrees Celsius minimum night and 25 degrees Celsius maximum day.

The following observations, measurements and comparisons describe plants grown in Salinas, Calif. under greenhouse conditions which approximate those generally used in commercial greenhouse practice.

The following traits have been repeatedly observed and are determined to be basic characteristics of Naples, which, in combination, distinguish this chrysanthemum as a new and distinct cultivar:

1. Flat capitulum form.
2. Decorative capitulum type.
3. Clear white ray floret color, with a cream flower center and cream flower buds.

4. Diameter across face of capitulum of 70 to 80 mm when fully opened.
5. Flowering response in Salinas under normal temperatures is 51 to 55 days after start of short days.
6. When grown in Salinas, the peduncle length of the first lateral at flowering after removing the apical bud without growth regulator applications is 10 to 15 cm, and the peduncle length of the fourth lateral at flowering is 15 to 20 cm.
7. Plant height is 81 to 86 cm when grown as a single stem cut mum in Salinas with 6 to 8 long days prior to start of short days.

The above measurements represent repeated flowerings over a period of a minimum of two years.

The accompanying photographic drawings show typical inflorescence and leaf characteristics of Naples, with the colors being as nearly true as possible with illustrations of this type.

Sheet 1 is a color photograph of Naples grown as a single stem cut spray mum.

Sheet 2 is a black and white photograph of three views of the inflorescence of Naples.

Sheet 3 is a black and white photograph showing the upper and under sides of the leaves of Naples at three stages of development (mature, intermediate and immature).

Of the commercial cultivars known to the inventor, the most similar in comparison to Naples is the unpatented cultivar Polaris, a white flat decorative cut spray mum. Reference is made to attached Chart A, which compares certain characteristics of Naples to the same characteristics of Polaris.

Similar traits are capitulum form and type and spray formation. Naples has a clear white flower color with a cream center, creating a two-tone effect, compared to the creamy white flower of Polaris. Naples also has a shorter plant height than Polaris. The peduncle length and the flowering response of both cultivars is comparable.

In the following description color references are made to The Royal Horticultural Society Colour Chart. The clear white ray floret color of Naples is not represented in the R.H.S. Colour Chart. The color values were determined on plant material grown in Salinas, Calif. on July 18, 1989.

Classification:

*Botanical.*—Dendranthema grandiflora cv Naples.
*Commercial.*—Decorative cut spray mum.

INFLORESCENCE

A. Capitulum:
*Form.*—Flat.
*Type.*—Decorative.
*Diameter across face.*—70 to 80 mm when fully opened.

B. Corolla of ray florets:
*Color (general tonality from a distance of three meters).*—Clear white, with a cream flower center, and cream buds.
*Color (upper surface).*—Clear white except for the center which is overcast with 9D to give a cream color effect.
*Color (under surface).*—Clear white.
*Shape.*—Straight, with a slight longitudinal petal twist, cross section flat, apex concave and slightly indented.

C. Corolla of disc florets:
*Color (mature).*—Closest to 2B.
*Color (immature).*—Closest to 151D.

D. Reproductive organs:
*Androecium.*—Present on disc florets only; very few disc florets, barely visible in the mature flower; scant pollen.
*Cynoecium.*—Present on both ray and disc florets.

PLANT

A. General appearance:
*Height.*—Plant height is 81 to 86 cm when grown as a single stem cut mum in Salinas with 6 to 8 long days prior to start of short days.

B. Foliage:
*Color (upper surface).*—147A.
*Color (under surface).*—147B.
*Shape.*—See photograph.

CHART A

COMPARISON OF NAPLES AND POLARIS

| CHARACTERISTIC | NAPLES | POLARIS |
|---|---|---|
| Ray floret color | White with cream center | Creamy white |
| Capitulum form | Flat | Flat |
| Capitulum type | Decorative | Decorative |
| Spray formation | Terminal | Terminal |
| Peduncle length | | |
| 1st lateral | 10 to 15 cm | 14 to 15 cm |
| 4th lateral | 15 to 20 cm | 18 to 20 cm |
| Diameter across face of capitulum | 70 to 80 mm | 76 to 83 mm |
| Plant height with 6–8 long days | 81 to 86 cm | 94 to 104 cm |
| Flowering response period | 51 to 55 days | 51 to 53 days |

COMPARISONS MADE OF PLANTS GROWN AS SINGLE STEM SPRAY CUT MUMS IN SALINAS, CALIFORNIA

I claim:

1. A new and distinct Chrysanthemum plant named Naples, as described and illustrated.

* * * * *

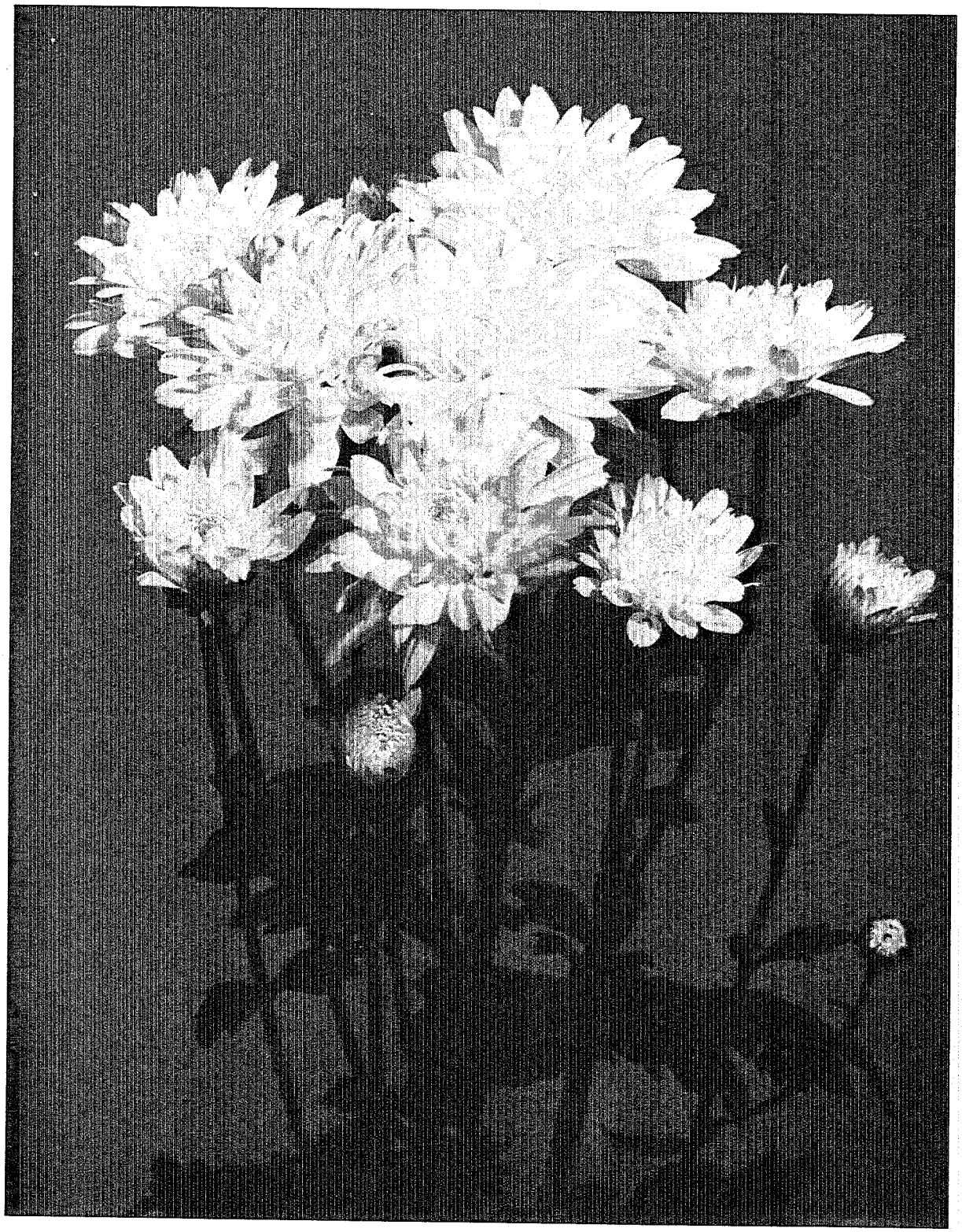

United States Patent Office

PTO - BOYERS, PA Duty Station

MISSING PAGE TEMPORARY NOTICE

PATENT # PLANT 7488 FOR ISSUE DATE 4-2-91

HAS BEEN SCANNED, BUT WITH MISSING PAGE(S). UPON RECEIVING OF MISSING PAGE(S), THE ENTIRE DOCUMENT WILL RE RESCANNED. PLEASE CALL IMAGE DATA ADMINISTRATION STAFF OF 557-6154 IF YOU HAVE A QUESTION. ASK FOR DAVE GROOMS, ANITA YOUNG OR POLA JONES.

THIS NOTICE IS FOR THE MISSING PAGE CONTAINING:

DRAWING SHEET # 2 + 3

N/A at Boyers
7/30/92

Data Conversion Operation

Boyers, Pa